United States Patent
Boyes et al.

(10) Patent No.: US 9,795,773 B2
(45) Date of Patent: Oct. 24, 2017

(54) MEDICAMENT UNIT DOSE CARTRIDGE AND DELIVERY DEVICE

(71) Applicant: Indosys Limited, Siddington, Cheshire (GB)

(72) Inventors: Robert Nichol Boyes, St Albans (GB); Philip Wilson Braithwaite, Cheltenham (GB)

( * ) Notice: Subject to any disclaimer, the term of this patent is extended or adjusted under 35 U.S.C. 154(b) by 416 days.

(21) Appl. No.: 14/365,996

(22) PCT Filed: Dec. 14, 2012

(86) PCT No.: PCT/GB2012/000907
§ 371 (c)(1),
(2) Date: Jun. 16, 2014

(87) PCT Pub. No.: WO2013/088112
PCT Pub. Date: Jun. 20, 2013

(65) Prior Publication Data
US 2014/0364837 A1    Dec. 11, 2014

(30) Foreign Application Priority Data

Dec. 16, 2011 (GB) .................................. 1121683.5
May 18, 2012 (GB) .................................. 1208854.8

(51) Int. Cl.
*A61M 15/00* (2006.01)
*A61M 31/00* (2006.01)
*A61M 15/08* (2006.01)
*B05B 7/14* (2006.01)

(52) U.S. Cl.
CPC ...... *A61M 31/007* (2013.01); *A61M 15/0028* (2013.01); *A61M 15/0043* (2014.02); *A61M 15/0066* (2014.02); *A61M 15/08* (2013.01); *B05B 7/1413* (2013.01); *A61M 2202/064* (2013.01); *A61M 2205/073* (2013.01); *A61M 2205/075* (2013.01)

(58) Field of Classification Search
CPC .............. A61M 15/0065; A61M 15/08; A61M 2202/064
USPC ........................................... 604/58
See application file for complete search history.

(56) References Cited

U.S. PATENT DOCUMENTS

| 7,305,986 | B1 * | 12/2007 | Steiner | .............. A61M 15/0028 128/203.12 |
| 8,551,067 | B2 * | 10/2013 | Zinger | .................. A61J 1/1406 604/403 |
| 2004/0025876 | A1 * | 2/2004 | Miller | .................. A61K 9/4816 128/203.15 |
| 2007/0272763 | A1 * | 11/2007 | Dunne | .................. A61M 11/02 239/8 |

FOREIGN PATENT DOCUMENTS

| JP | 2005253882 | 9/2005 |
| WO | WO2005023348 | 3/2005 |
| WO | WO2008051621 | 5/2008 |

* cited by examiner

*Primary Examiner* — Kevin C Sirmons
*Assistant Examiner* — Deanna K Hall
(74) *Attorney, Agent, or Firm* — Simana Rao, Esq.; McNeely, Hare & War LLP (57) ABSTRACT

There is described a dry powder medicament delivery device comprising: a medicament container containing a unit dose of dry powder medicament; a medicament dispensing assembly; and optionally an air source.

16 Claims, 9 Drawing Sheets

MEDICAMENT UNIT DOSE CARTRIDGE AND DELIVERY DEVICE

CROSS-REFERENCE TO RELATED APPLICATIONS

This application is a National Phase Application under 35 USC 371 of PCT/GB2012/000907, filed Dec. 14, 2012 (published as WO 2013/088112), which claims priority to British Application No. 1121683.5, filed on Dec. 16, 2011, and British Application No. 1208854.8, filed on May 18, 2012. The disclosures of the prior applications are considered part of and are incorporated by reference in their entirety in the disclosure of this application.

FIELD OF THE INVENTION

The present invention relates to novel dry powder medicament delivery device, uses thereof and methods of manufacture.

More particularly, the invention relates to novel dry powder medicament delivery device which is suitable for use as, for example, a nasal medicament delivery device for the delivery of medicaments, e.g. for the treatment of a respiratory disorder and especially for the delivering of a vaccine or a hormone, such as, glucagon, in dry powder form. The medicament delivery device is also suitable for use for the delivery of a medicament in, e.g. in powder form, into an infusion bag, the medicament then being delivered to the patient as a fluid infusion, for example, as an 'IV drip'.

The invention also relates to a novel medicament carrying cartridge for use in a medicament delivery device.

BACKGROUND TO THE INVENTION

In recent years drug formulations have been developed in dry powder form, e.g. for delivery by inhalation, or by admixing in a solution for delivery by intravenous infusion. Such dry powder formulations include existing compounds reformulated into dry powder form and newly developed compounds, used in the treatment of many conditions and diseases.

Drug formulations in the form of inhaled dry powders offer advantages over other forms such as liquids and tablets, particularly when considering storage and stability.

Oral or nasal delivery of a medicament using a dry powder medicament delivery device is a particularly attractive method of drug administration as such devices can be relatively easy for a patient to use. As well as delivering medicament to treat local diseases of the airway and other respiratory disorders, dry powder medicament delivery devices have more recently also be used to deliver drugs to the bloodstream via the lungs or nasal passages, thereby avoiding, for example, the need for injections.

One advantage of delivering a drug in a dry powder form is that very low dosages of the medicament may be used. However, in many situations the disadvantage of using dry powder formulations lies in the complication of actual delivery to the patient's area of treatment and/or the metering of very low dosages of medicament. The principle problem lies in the accurate metering and containment of a unit of dose and subsequent appropriately controlled release or dispensing of the unit dose. This is a significant impediment for the pharmaceutical industry in developing the potential of dry powder formulations to end products.

Dry powder delivery devices are most commonly known in the form of dry powder inhalers, these range from metered dose devices such as Clickhaler® where the dry powder medicament is stored in a reservoir and metered by operation of the device; to unit dose devices where the medicament is stored in individual unit doses in capsules (e.g. Spinhaler®) or foil blisters (e.g. Diskhaler®). These devices are generally cumbersome and complex in construction and, although suitable for their intended use for delivering medicament to the lung, their adaption for delivery to other areas of treatment, such as the nasal passage and/or nasal cavity, is generally unsatisfactory.

Furthermore, for delivery of a dry powder medicament by way of an intravenous infusion, the process of admixing a powdered drug to an infusion bag can involve the following steps:

Drawing a specified volume of the infusion fluid into a syringe.

With a needle on the syringe injecting the infusion solution into a rubber stoppered vial containing the weighed amount of powdered drug substance.

Mixing the infusion solution with the powdered substance

Drawing the powder mixture or solution of drug back into the syringe

Transferring the mixture/solution from the syringe into the large volume injection solution usually contained in a flexible plastic bag.

However, there are a number of problems associated with this procedure;

The process can be cumbersome involving several steps

Needles are involved to facilitate injection into the vial containing drug

Storage may be an issue because the drug vial needs to have enough capacity to accommodate the fluid volume Dosage errors may be created in the transferring process Handling of chemotherapy drugs may be complicated by the transferring process.

The present invention seeks to provide a dry powder medicament delivery device that overcomes or substantially alleviates the problems with conventional inhalation devices and/or infusion devices. In particular, the invention seeks to provide a device having a significantly simpler construction than known devices. The dry powder medicament delivery device of the present invention is also easier to manufacture, assemble and operate, as well as being cheaper to manufacture.

The present invention now described offers a means of metering a unit dose of dry powder into a container or cartridge that is readily adaptable to a range of devices designed to suit a diverse range of treatment types. One advantage is that of the delivery device of the present invention is that it is capable of accurately delivering a metered dose of a powdered medicament and is easy to operate, inexpensive and disposable.

A further advantage of the present invention is that the method of metering/filling the dry powder into the unit dose container or cartridge is capable of being easily scaled from laboratory hand filling to mass production.

Furthermore, recently dry powder intranasal vaccines have been developed. There are a number of advantages to intranasal delivery of drugs, in particular in dry power form. Intranasal drug delivery offers rapid uptake into the blood stream by absorption through the nasal mucus, the potential to reduce or eliminate cold chain management of vaccines during storage and transportation, and the elimination of needles and the potential for needle stick injuries.

Intranasal vaccination represents an attractive non-invasive alternative to needle-based injection and provides superior protection at mucosal surfaces. However, new formulations and delivery devices are needed to improve efficacy and reduce the refrigerated storage and distribution requirements associated with standard liquid vaccines.

Vaccines formulated as liquids can be subject to chemical degradation, e.g., aggregation, denaturation, hydrolysis, and oxidation that can result in their inactivation. Liquid vaccine formulations can also be sensitive to temperature: high temperatures can increase inactivation, and freezing temperatures can result in ice that can damage antigen in the vaccine. Thus, to prevent inactivation, liquid vaccines often must be stored at a temperature range of from 2-8° C.

The mode of administration of a vaccine can play a role in its efficacy. One mode of administration, non-parental administration (e.g., nasal), can induce and promote mucosal and systemic immune responses. In addition, nasal mucosa can help bind a virus or other pathogen at the mucosal surface, preventing access of the pathogen to deeper tissues and/or decreasing the likelihood of full-blown infection.

A yet further advantage of the delivery device of the present invention is the use of a novel medicament carrying cartridge. US Patent application No. 2007/060868 and U.S. Pat. No. 6,398,074 describe medicament delivery devices which, when actuated, deliver a medicament powder with a generally linear flow. Such devices will generally suffer from a lack of deagglomeration of the powder. This contrasts with the novel medicament carrying cartridge hereinafter described which provides a non-linear pathway for the powder, aiding, inter alia, deagglomeration.

SUMMARY OF THE INVENTION

Therefore, according to a first aspect of the invention there is provided a dry powder medicament delivery device comprising:
 a medicament container, e.g. a cartridge, containing a unit dose of dry powder medicament;
 a medicament dispensing assembly; and
 optionally an air source According to a further aspect of the invention the dry powder medicament delivery device includes an air source.

The medicament container may comprise a unit dose drug container or cartridge comprising an elongate member provided with an inset cavity which acts as a medicament reservoir and a closure sleeve. Such a container or cartridge is hereinafter described in more detail and with references to FIGS. 7a to 7c herein.

An important aspect of the cartridge comprising an elongate member and slidable outer sleeve is that, in use, the medicament powder is caused to flow in a non-linear pathway before being expelled from the delivery device. Indeed, the cartridge of this aspect of the invention is such that the medicament powder is caused to substantially flow via at least two angular turns, e.g. right angled turns, i.e. a first right angle turn followed by a second right angle turn as it is expelled from the delivery device. Preferably, two angular turns are present. This provides a significant advantage in efficiently deagglomerating the powder whilst not impeding the efficient clearing of the entire dose from the drug cavity of the cartridge with sufficient velocity for the powder to reach its intended target, for example, the nasal cavity. Furthermore, the elongate member and slidable outer sleeve provides a simple secure storage compartment for the powdered medicament which, when activated, also provide an effective means of powder deagglomeration as hereinbefore described.

However, although a cartridge comprising an elongate member and slidable outer sleeve is to be preferred, it will be understood by the person skilled in the art that a variety of known unit dose medicament containers may suitably be used in the dry powder medicament delivery device. Thus, for example, the unit dose dry powder formulation may comprise a pre-packaged capsule or blister, which each contains an individual dose, usually in the form of dose of the powder, which has been accurately and consistently measured.

A medicament dispensing assembly generally comprises a body and a nozzle. More particularly, the medicament dispensing assembly comprises a body, a nozzle and airways, e.g. two airways, an inlet and an outlet. For an intranasal delivery device, the nozzle is desirably sized and shaped to be suitable for placing inside a patients nostril. Although it will be understood by the person skilled in the art that the medicament dispensing assembly may also be designed so as to be suitable for oral delivery, such as an inhaler for delivery to the lungs (respiratory tract). For intravenous delivery, e.g. via an infusion bag, the medicament dispensing assembly comprises a body, a nozzle, an inlet and an outlet, wherein the outlet comprises means for connecting to a fluid bag, e.g. an infusion bag.

The air course may comprise a delivery pump e.g. it may comprise a syringe. Such a syringe may, for example, comprise a conventionally known propriety syringe, e.g. a disposable syringe, or may comprise a conventionally known means for ejecting an air stream, for example, an insufflator or other such apparatus suitable for blowing air or gas upon activation, such as a cylinder and piston, bellows, a squeezable bulb or a compressed air or gas source such as a compressed air canister or from a compressed air system fitted with suitable volume and pressure control apparatus.

Alternatively, in a further embodiment for use as a nasal medicament delivery device, the syringe may be replaced with a tube, so formed that the patient can place the open end between their lips and blow the dry powder drug into their nasal cavity.

In a yet further embodiment, the syringe may be replaced with a drinking straw and the nozzle may be replaced with an alternative nozzle so shaped to facilitate the user being able to suck liquid though the device entraining the dry powder drug into the liquid. It will be understood by the person skilled in the art that the medicament powder may be entrained in any suitable liquid, for example, an aqueous carrier, including, but not limited to, a gel.

In particular with the intranasal delivery device of the invention it is desirable that the velocity of the air and the volume of air that passes through the device should be controlled. Therefore, it may be desirable to utilise a dedicated air velocity/volume control system instead of a regular syringe. Such a dedicated air dedicated air velocity/volume control system may comprise a dedicated (air) pump. Alternatively, a dedicated air velocity/volume control system may comprise a bursting diaphragm or a dispensing valve. Furthermore, the use of a resiliently flexible diaphragm valve member, or bursting diaphragm, may be advantageous in that by positioning a dispersible dry powder material, e.g. a medicament material, downstream of a resiliently flexible diaphragm valve member or bursting diaphragm; causing the valve member to flex, or the diaphragm to burst, will produce a rapid depletion of the air pressure up-stream of the valve or diaphragm through the air-path in the device that disperses and/or deagglomerates the material.

When the delivery device comprises a dry powder inhaler, e.g. an intranasal inhaler, an air source may be provided. Although it will be understood by the person skilled in the art that the air source may comprise a syringe. Furthermore, a bursting diaphragm or dispensing valve may, for example, be fitted between the air source and the (intranasal) delivery device so that when the diaphragm bursts or ruptures or the dispensing valve opens at a certain predetermined air pressure the velocity of the air rushing through the device will clear it very effectively. For example, air from a bursting diaphragm is likely to disperse the powder twice the distance than the same volume of air from a syringe being depressed quickly by hand.

Thus according to the invention we provide a method of producing an aerosol of a dry powder which comprises positioning a dispersible dry powder material, e.g. a medicament material, downstream of a resiliently flexible diaphragm valve member or bursting diaphragm; wherein causing the valve member to flex or the diaphragm to rupture will produce a rapid depletion of the air pressure up-stream of the valve or diaphragm through the air-path in the device that disperses and/or deagglomerates the material.

The resiliently flexible dispensing valve may comprise a resiliently flexible diaphragm valve member. Such a valve member is described in EP 0 160 336. European Patent Application No. 0 160 336 describes a flexible container e.g. a shower gel container including a self-sealing dispensing valve. Generally, the valve comprises a flexible resilient diaphragm with at least one slot. This valve is closed until pressure is applied to the flexible container which causes the valve to take up a convex shape and the slit opens. The self-sealing valve described in the prior art is known to be used in, for example, containers for storage and dispensing of gels and/or viscous liquids since the resilient valve member will close when pressure is removed from the walls of the dispensing container. Such a valve is ideally suited for dispensing devices which are inverted in use.

Thus, the preferred valve comprises a resiliently deformable, concave shaped portion with its perimeter optionally sealingly secured across a discharge orifice. The valve, which will generally be self-sealing, may be secured across an orifice so that it is in a closed position. The valve may be placed in an arrangement whereby it is inwardly concave or, alternatively, it may be outwardly concave when in the closed position. The concave shaped portion of the valve may include at least one substantially linear slit extending through the thickness of the wall that comprises the concave portion of the valve. The valve requires the attainment of a threshold opening pressure to effect inversion from the concave, at rest, position in order to dispense the material. When opened, the valve will generally move to a convex arrangement, thus the valve may present an outwardly facing convex surface or an inwardly facing convex surface when open.

The circumferential wall of the valve member may be provided with a plurality of circumferential spaced apart pimples on the inside surface of the wall. The pimples are especially advantageous in the embodiment in which the valve is in an inwardly concave position at rest and an inwardly convex position when open. Thus, when the valve is urged to an open position, the pimples may react against distortion of the side wall and therefore urge the valve back to a closed position. Thus a pressure differential is essential to reopen the valve member of the invention.

Many different materials may be used as the diaphragm valve member. The material may vary depending upon the nature of the material intended to pass through the valve. Most importantly it should be a flexible, resilient and/or elastomeric. The material may preferentially be non-porous. More particularly when the valve mechanism is used such that it is actuated by a gas pressure differential, then the membrane material should be non-gas permeable. Thus, plastics materials are well suited for use as the valve member material, an elastomer such as silicone rubber being one example of such a plastics material. Other examples include, but are not limited to, polyvinyl chloride, urethane, ethylene vinyl acetate and styrene butadiene copolymer.

It will be understood by the person skilled in the art that the resiliently flexible dispensing valve may be replaced by a bursting diaphragm (not illustrated). Such a bursting diaphragm may comprise a frangible membrane, e.g. a plastic membrane, which is adapted to rupture under pressure. Such a bursting diaphragm assembly is especially suited for use with a disposable device, since it would be suitable for a once only operation. This contrasts with a device comprising a resiliently flexible dispensing valve member which can be operated repeatedly.

In one embodiment, the dry powder medicament delivery device comprises a medicament delivery device, e.g. a nasal inhaler. However, in a further embodiment drug carrier is utilised in a device to facilitate application of the drug in dry powder form via an air flow to the vagina or rectum, such a device may be fitted with a means to dilate the vagina or rectum.

The dry powder medicament delivery device according to this aspect of the invention may be suitable for delivery of a variety of medicaments and may be suitable for use in the treatment of a variety of disorders.

Thus, for example, for use as an inhaler, e.g. an inhaler for oral drug delivery, or a nasal dry powder medicament delivery device, e.g. a nasal inhaler, a variety of medicaments may be administered. Such medicaments are generally suitable for the treatment of asthma, COPD and respiratory infections. Such medicaments include, but are not limited to [beta] 2-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratropium bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide, flunisolide and ciclesonide, and isomers and/or salts or derivatives thereof.

Specific combinations of medicaments which may be mentioned include combinations of steroids, such as, beclomethasone dipropionate and formoterol; beclomethasone dipropionate and salmeterol; fluticasone and formoterol; fluticasone and salmeterol; budesonide and formoterol; budesonide and salmeterol; flunisolide and formoterol; and flunisolide and salmeterol. It is also within the scope of this invention to include combinations of one or more of the aforementioned steroids with one or more of the aforementioned β2-agonists.

However, there is increasing interest in the pulmonary delivery or intravenous delivery of medicaments due, inter alia, to the rapid onset of their efficacious effect. Thus, further medicaments which may be mentioned include systemically active materials, such as, proteinaceous compounds and/or macromolecules, for example, hormones and mediators, such as insulin, glucagon, human growth hormone, leuprolide and alpha interferon, growth factors, anticoagulants, immunomodulators, cytokines and nucleic acids. Other medicaments which may be mentioned are those for the treatment of neurological disorders, such as Parkinsonism, such as, levodopa, carbidopa, benserazide, selegiline, tolcapone, entacapone, bromocriptine, lysuride, pergolide, ropinirole and cabergoline; or migraine, such as divalroex sodium, ergotamine, methysergide, metoprolol, propranolol, zolmitriptan, vigabatrine, clonidine, ganaxolone, lysine acetylsalicylate, sumatriptan, naratriptan, timolol, almotriptan, cyproheptadine, rizatriptan, timotol, dotarizine, dihydroergotamine, metysergide, pizotifen, eletriptan, prochlorperazine, nadolol and frovatriptan. In addition, medicaments for the treatment of sexual dysfunction may be mentioned. Such disorders include erectile dysfunction where treatments include administration of phosphodiesterase type-5 (PDTE5) inhibitors, such as tadalafil, vardenafil and sildenafil; and premature ejaculation, where treatments include administration of selective serotonin reuptake inhibitors, such as dapoxetine.

However, one particular aspect of the present invention provides the dry powder medicament delivery device as hereinbefore described as a nasal dry powder medicament delivery device. A nasal dry powder medicament delivery device according to this aspect of the invention may be suitable for the delivery of any of the medicaments hereinbefore described.

Another particular aspect of the present invention provides the medicament delivery device as hereinbefore described as intravenous delivery device or, more particularly, a device for measuring a desired dose of medicament suitable for intravenous delivery, for example, via a fluid bag, e.g. an infusion bag.

An important use of the delivery device of the present invention is for the delivery of an emergency therapy. The intranasal or intravenous route of drug delivery can afford rapid absorption of drugs into the blood circulation. For example, the intranasal route can also offer a less invasive route of drug administration compared with some other routes such intravenous or intramuscular injection. Such rapid and effective drug delivery can be useful in the treatment of crisis situations such as pain, convulsions, serious hypoglycaemic reaction, etc.

The delivery device of the present invention is found to be especially advantageous in the delivery of a medicament in an emergency situation, for example, where the patient is unconscious. The nasal delivery device of the invention is especially useful in a situation where medical staff are not available. One specific such therapy is the intranasal administration of a therapeutically effective amount of glucagon to a diabetic who is experiencing a serious hypoglycaemic reaction. Glucagon is a hormone that causes the liver to release glucose into the blood and is used to quickly increase blood sugar levels in diabetics with hypoglycaemia (low blood sugar). Glucagon is usually provided in powder form and given as an injection either into a vein, an arm or leg muscle or under the skin as directed, usually to an unconscious patient. The glucagon powder must first be dissolved in a diluting fluid and must be used immediately after it has been mixed.

Therefore, according to a particular aspect of the present invention there is provided a method of delivering glucagon to a patient which comprises the use of a medicament delivery device as hereinbefore described, especially the use of a dry powder nasal dry powder medicament delivery device.

A further category of patients for whom intravenous or intramuscular injection may be problematical is infants and young children, therefore the use of the delivery device of the present invention as an intranasal, oral or rectal drug delivery device may be beneficial.

In addition, when used as an inhaler, e.g. an oral inhaler and especially a nasal dry powder medicament delivery device, the medicament delivery device as hereinbefore described may suitably be used for the delivery of one or more dry powder vaccines.

Dry powder vaccine compositions for intranasal delivery are described in International Patent application No. WO 2011/129120. Therefore, a dry powder vaccine for use in association with a medicament delivery device, such as a nasal dry powder medicament delivery device, of the present invention, can be useful for the prevention and/or treatment of infection by any virus.

However, it will be understood by the person skilled in the art that the dry powder medicaments mentioned herein can be delivered using the delivery device of the present invention, to deliver a dry powdered medicament to, for example, an intravenous infusion bag.

In a further embodiment a medicament carrier may be utilised in a device to facilitate application of the medicament in dry powder form, by entraining the powder in a gel for administration to a body orifice.

In a yet further embodiment a medicament carrier may be utilised in a device to facilitate dermal or transdermal application of the drug in dry powder form, via a gel applicator.

It will be appreciated that the above descriptions can apply to the treatment of animals as well as humans.

The preferred unit dose medicament container e.g., a cartridge, for use in association with the dry powder medicament delivery device of the present invention is novel per se.

The invention further provides a method of delivering a medicament, e.g. a dry powder medicament, to a patient which comprises the use of a dry powder medicament delivery device as hereinbefore described.

When the method according to this aspect of the invention comprises intravenous drug delivery, the method may include a process of admixing a powdered medicament into an infusion bag, e.g. an intravenous infusion bag. An exemplary process may include, by way of illustration only, involves the following steps:

The main body is first connected to a bag of fluid bag (directly or via a connecting tube). Fluid is prevented from flowing from the bag by the use of a stop cock or clamp.

A syringe is connected at the opposite end of the main body.

The drug or medicament carrier is moved to its open position.

The stop cock/clamp is opened, allowing fluid to flow from the bag.

The syringe plunger is drawn back and in the process draws fluid from the fluid bag, entraining and mixing the powder into the fluid.

The syringe plunger is depressed passing the powder/fluid mix back through the main body/drug carrier into the fluid bag Fluid may be prevented from leaking from the device by a seal which has a circumferential seal feature to seal against a seal housing within the main body and a face seal feature to seal against the face of the medicament carrier.

The invention further provides a method of treatment of a patient with a disorder which comprises the administration of a medicament using a medicament delivery device as hereinbefore described.

The method of treatment according to this aspect of the invention may comprise the administration of any one or more of the therapeutically active agents described herein.

However, there is especially provided a method of delivering a vaccine, e.g. a dry powder vaccine to a patient.

More especially, the invention provides a method of treating a patient which comprises the administration of a therapeutically effective amount of glucagon to a diabetic experiencing a hypoglycaemic reaction.

Therefore, according to a further aspect of the present invention there is provided a unit dose medicament container comprising an elongate member provided with an inset cavity; and a slidable outer sleeve.

The slidable outer sleeve is capable of sliding to either close or to reveal some or the entire cavity. As hereinbefore described, the unit dose medicament container is generally suitable for delivery of a dry powdered medicament, for example, to a dry powder nasal inhaler or an intravenous infusion bag.

Although the elongate member and slidable outer sleeve may comprise a variety of suitable materials and may be made by a variety of methods, and the member and sleeve may optionally comprise the same material e.g. a plastics material.

Desirably the elongate member comprises a suitable first plastics material and the slidable sleeve comprises an alternative second plastics material. The preferred device, i.e. comprising first and second plastics materials may be manufactured by a variety of methods, including, preferably a method known as two shot moulding. The two shot moulding method is a process of moulding that allows the combined components, i.e. the member (first plastics material) and sleeve (second plastics material) to be produced in a single machine cycle with no subsequent assembly. Such a method produces clear savings on economy.

The term 'suitable' plastics material as hereinbefore described is intended to mean, for example, first and second plastics material that do not to bond to each other. The lack of bonding between the first and second plastics material allows the sleeve to slide over the elongate member.

Thus, according to a further aspect of the invention there is provided a method of two shot moulding a medicament container comprising an elongate member comprising a suitable first plastics material and the slidable sleeve comprises an alternative second plastics material.

The unit dose medicament container as hereinbefore described is advantageous in that, inter alia, it is easy and economic to manufacture and can be easily filled either on an individual basis or in a fast moving production line. One method of filling is described in the specific embodiments herein.

According to a further aspect of the invention there is provided a dry powder medicament delivery device kit comprising:

a medicament container, e.g. a cartridge, containing a unit dose of dry powder medicament;

a medicament dispensing assembly; and optionally an air source.

In one aspect of the invention the kit comprises an air source. The air source of the kit as hereinbefore described may comprise a delivery pump, such as a syringe or a bellows, etc.

The kit according to this aspect of the invention may optionally include a dry powder inhaler. Alternatively, the kit may optionally include an intravenous infusion bag.

The invention will now be described by way of example only and with reference to the accompanying drawings in which

FIG. 11a is a cross-sectional view of the medicament delivery device for use in infusion, the device being in the closed position; and FIG. 11b is a cross-sectional view of the medicament delivery device for use in infusion, the device being in the open position.

Referring to FIGS. 1a to 1c, 2a to 2c and 7a to 7c, a dry powder medicament delivery device 1 comprises a medicament container 2 containing a unit dose of dry powder medicament 12, a medicament dispensing assembly 3 and optionally a syringe 4. The dispensing assembly 3 comprises a body 5, a nozzle 6 and airways 7 and 8. The medicament container 2 comprises a member 9, cavity 10 and sleeve 11.

To administer a dry powder medicament vaccine user (patient or medical person), connects a syringe 4, first extending the syringe 4 to its open (required capacity) position, to the dispensing assembly 3. The nozzle 5 is then depressed towards the syringe 4 and in doing so pushing the member 9, through the sleeve 11, to align the cavity 10, with the airways 7 and 8. The nozzle 6 is inserted into the patient's nostril (not shown) and the syringe 4 depressed, forcing air through airway 8 and cavity 10, entraining the dry powder medicament 12 and through airway 7 into the patient's nasal cavity (not shown).

The device in its preferred embodiment, is a single use device, the device may therefore be a disposable device which is discarded after use.

Figure 7A:
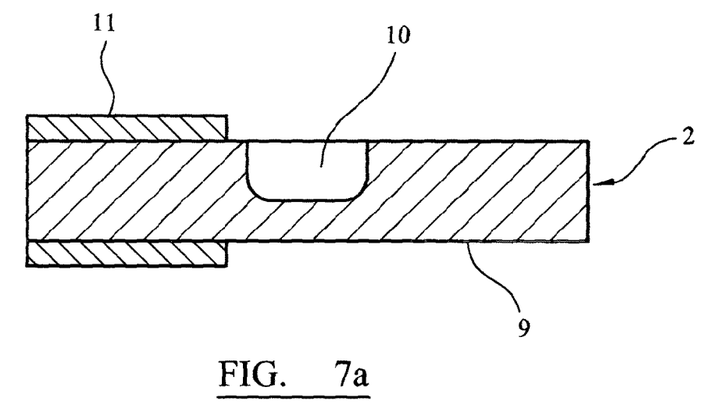
FIG. 7a is a cross-sectional view of the unit dose medicament container in the open position.
Figure 7B:
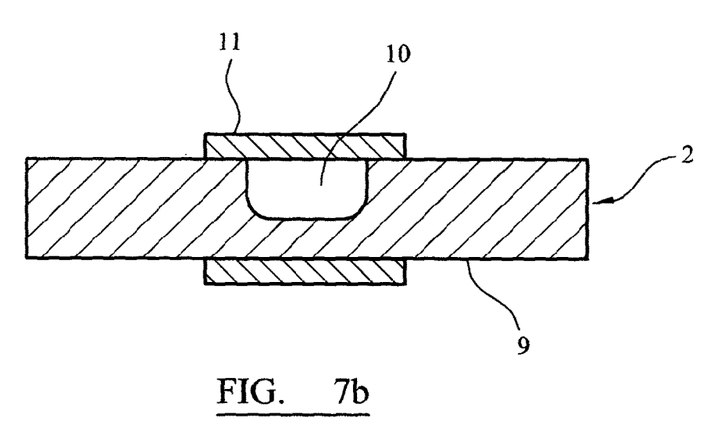
FIG. 7b is a cross-sectional view of the unit dose medicament container in the closed position.
Figure 7C:
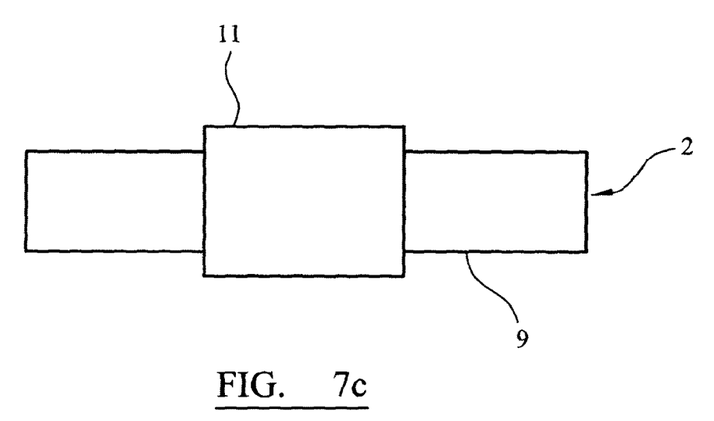
FIG. 7c is a side view of the unit dose medicament container in the closed position.
Figure 8A:
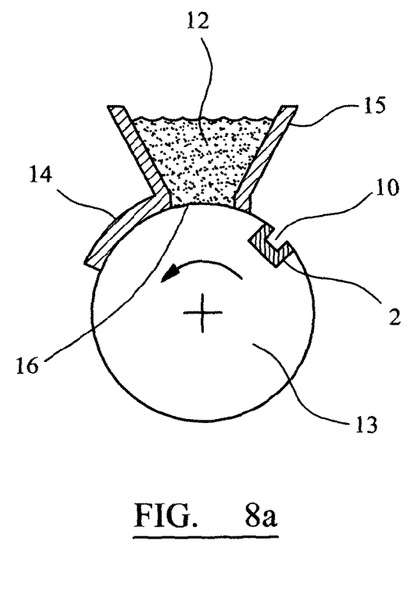
FIGS. 8a to 8d are schematic representations of the unit dose medicament container being filled.
Figure 8B:
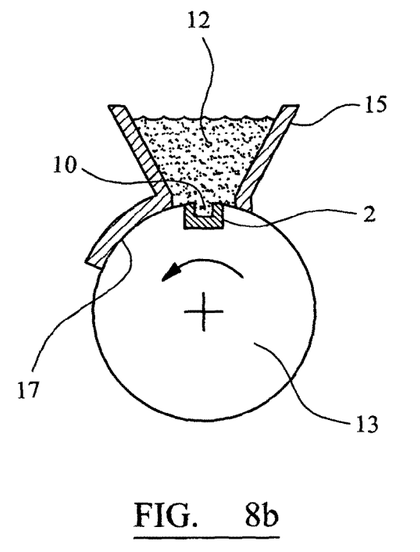
Figure 8C:
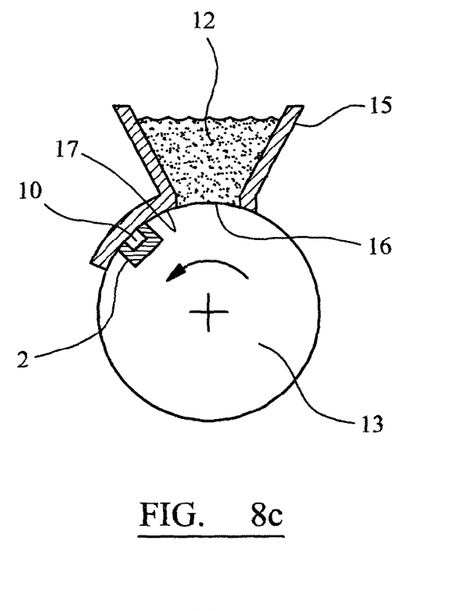
Figure 8D:
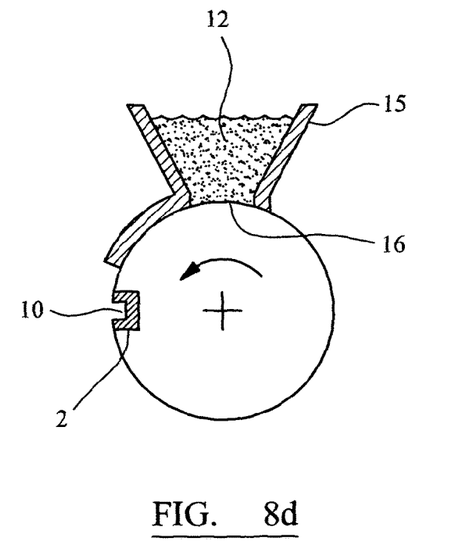
Figure 9A:
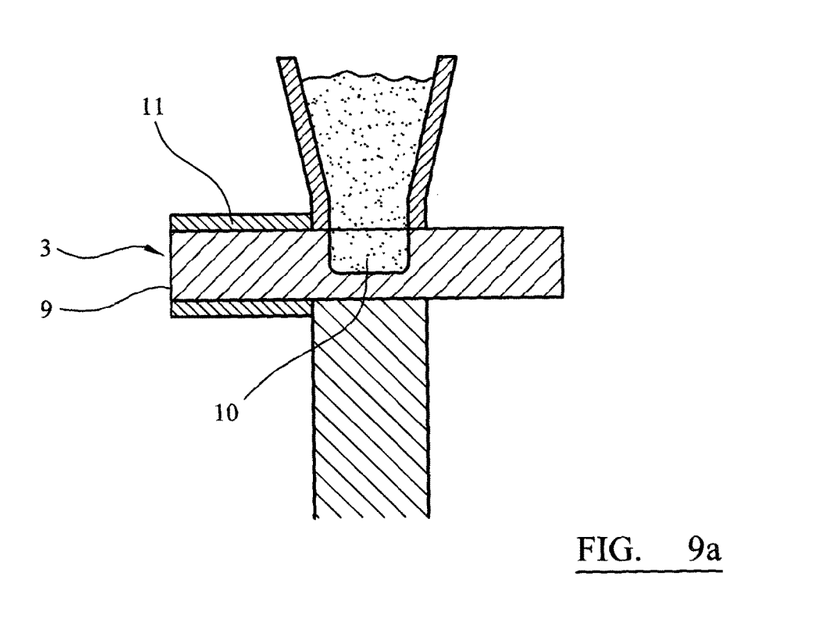
FIGS. 9a and 9b are schematic cross-sectional representations of the unit dose medicament container being filled.
Figure 9B:
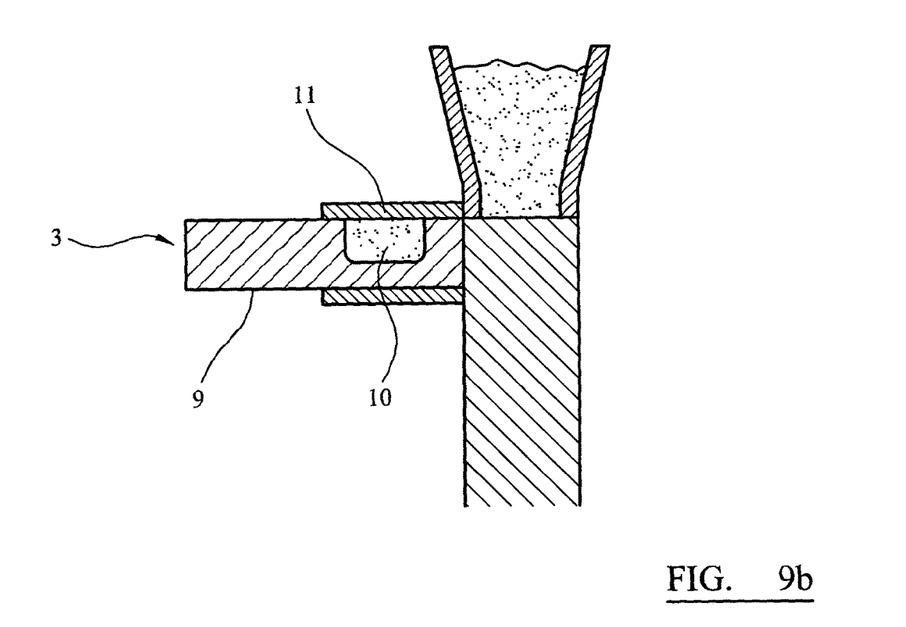

Referring to FIGS. 7a-c, the unit dose drug container 2, or cartridge, comprises a member 9 in which a cavity 10 is inset; a sleeve 11 is positioned on member 9. Member 9 is produced in a suitable polymer and the sleeve 11 is produced in an alternative suitable polymer, in a method known as two shot moulding, this process of moulding allows the combined component (member 9 & sleeve 11) to be produced in a single machine cycle with no subsequent assembly, producing clear economic savings.

Figure 1A:
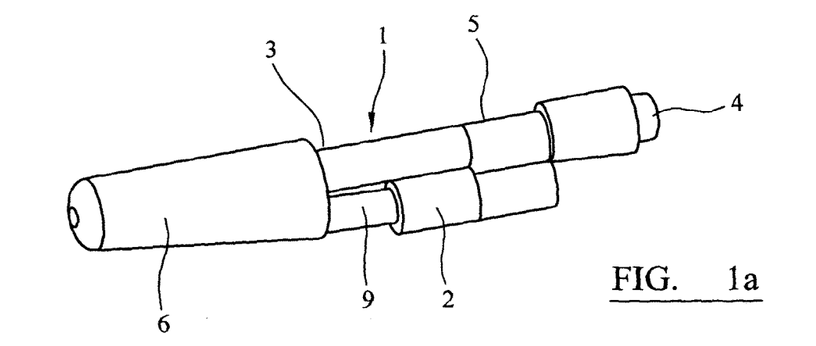
FIG. 1a is a perspective view of the medicament delivery device of the invention.
Figure 1B:
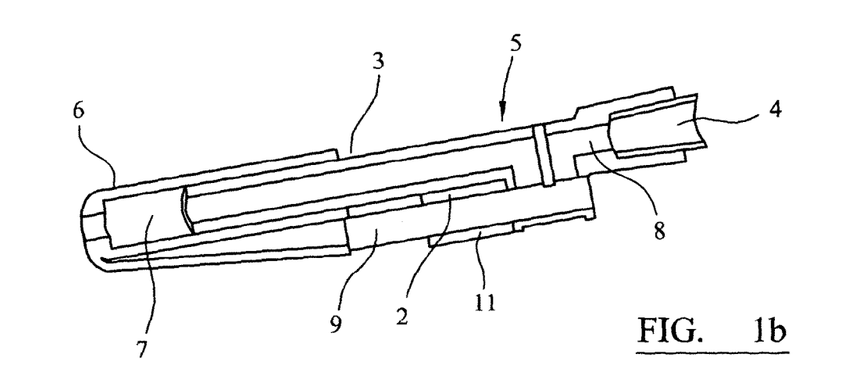
FIG. 1b is a cross-sectional view of the medicament delivery device.
Figure 1C:
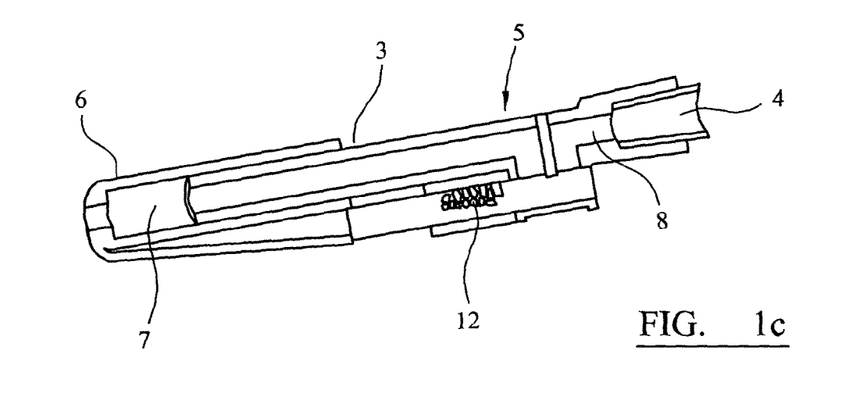
FIG. 1c is a cross-sectional view of the medicament delivery device with dry powder medicament present.
Figure 2A:
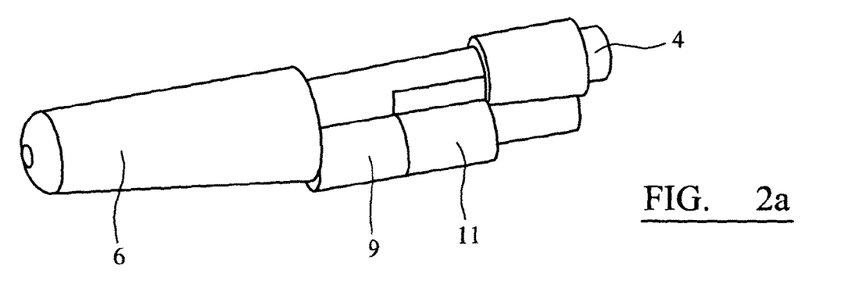
FIG. 2a is a perspective view of the medicament delivery device in the primed position.
Figure 2B:
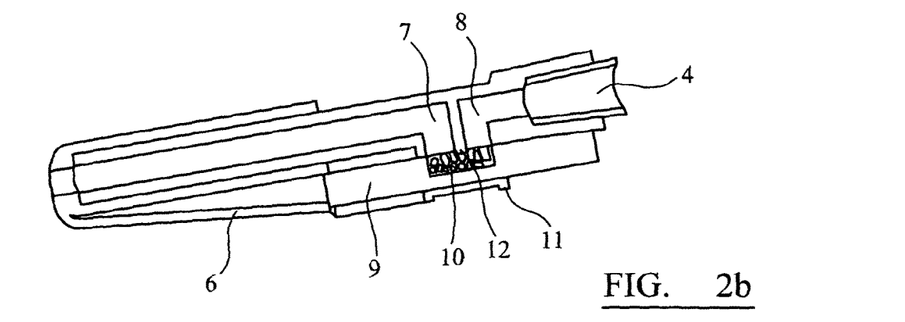
FIG. 2b is a cross-sectional view of the medicament delivery device in the primed position with dry powder medicament present.
Figure 2C:
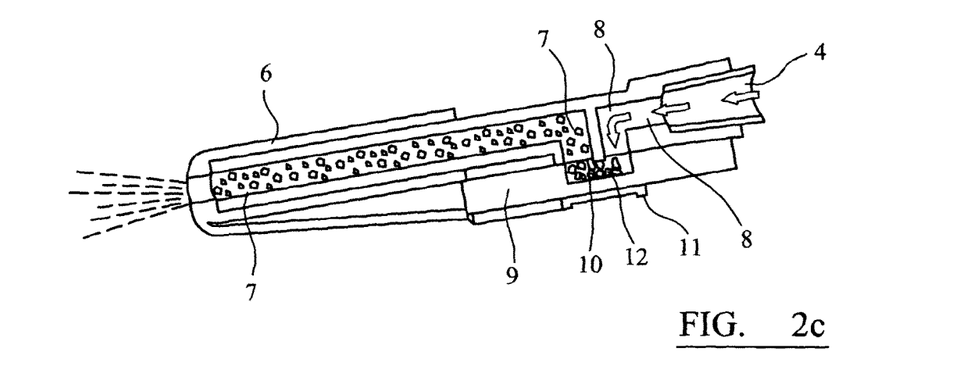
FIG. 2c is a cross-sectional view of the medicament delivery device being actuated.
Figure 3:
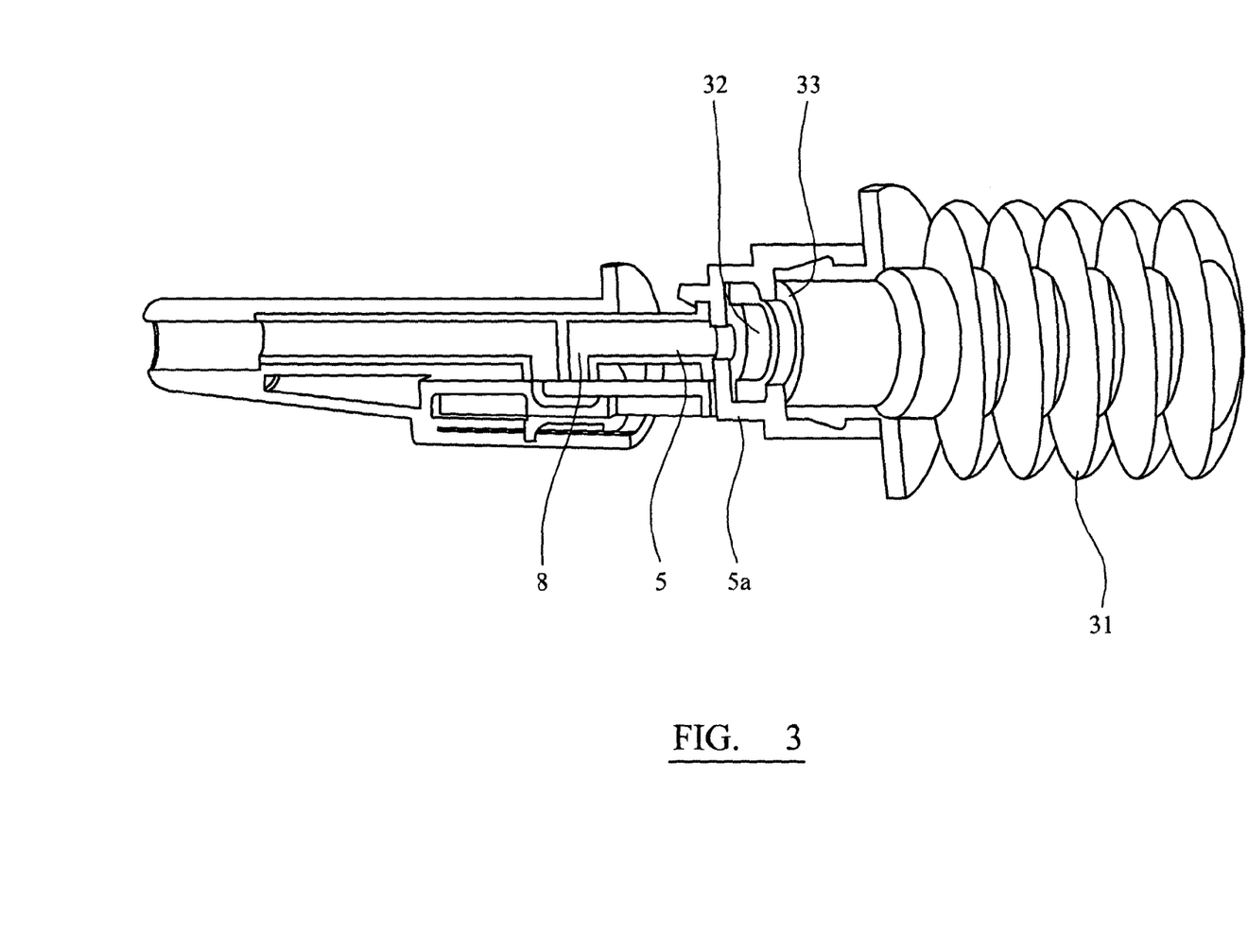
FIG. 3 is a cross-sectional view of the medicament delivery device employing a bellows fitted with a dispensing valve.

Referring to FIG. 3 body 5 is modified to incorporate feature 5a to house dispensing valve 32 retained by collar 33 and also retaining bellows 31, when the bellows 31 is depressed sufficiently to create the requisite pressure valve 32 opens releasing air at high velocity into airway 8.

Figure 4A:
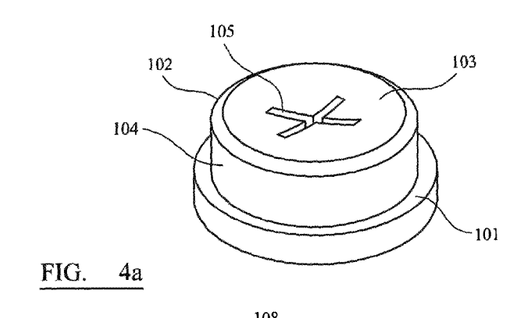
FIG. 4a is a perspective drawing of a valve of the invention in the closed position.
Figure 4B:
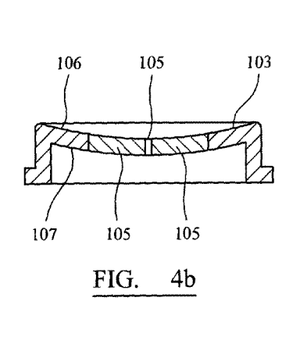
FIG. 4b is a cross-sectional view of a valve of the invention in the closed position.

With reference to FIGS. 4a and 4b, a diaphragm valve (101) comprises a circular peripheral flange (102) surrounding a concave valve member (103). The flange is connected to an annular portion (104). The concave valve member (103) comprises a flexible material and is provided with a slit (105) or a pair of slits in its body. The version illustrated shows a pair of slits in the form of a cross, although it will be appreciated that a variety of slit arrangements may be suitable for the invention to perform satisfactorily. The concave valve member (103) is provided with a dispensing surface (106) and a non-dispensing surface (107). Generally the dispensing surface (106) is the upper surface and the non-dispensing surface (107) is the lower surface.

Figure 5:
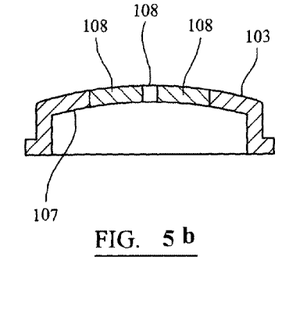
FIG. 5a is a perspective drawing of a valve of the invention in the open position.
FIG. 5b is a cross-sectional view of a valve of the invention in the open position.
Figure 5A:
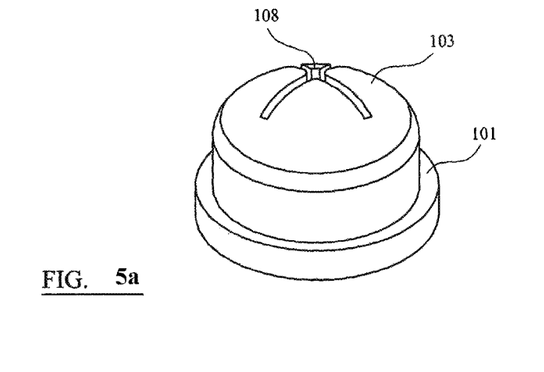

Referring to FIGS. 5a and 5b, when the valve (101) is actuated pressure is applied either directly or indirectly to the non-dispensing surface (107) of the valve member (103). This causes the concave valve member (103) to flex and take up a concave form. The slit (105) opens to create an aperture (108).

Figure 6A:
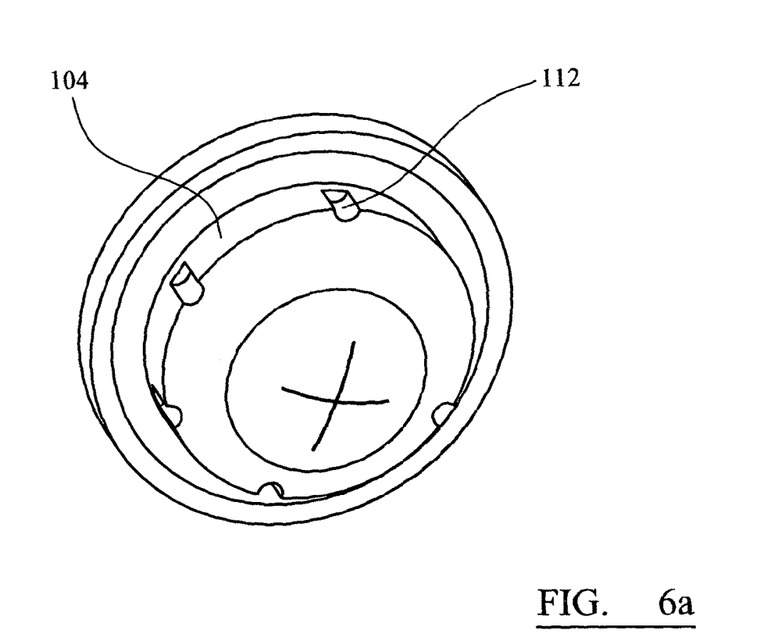
FIGS. 6a and 6b are perspective views of a valve of the invention illustrating the pimples on the valve.
Figure 6B:
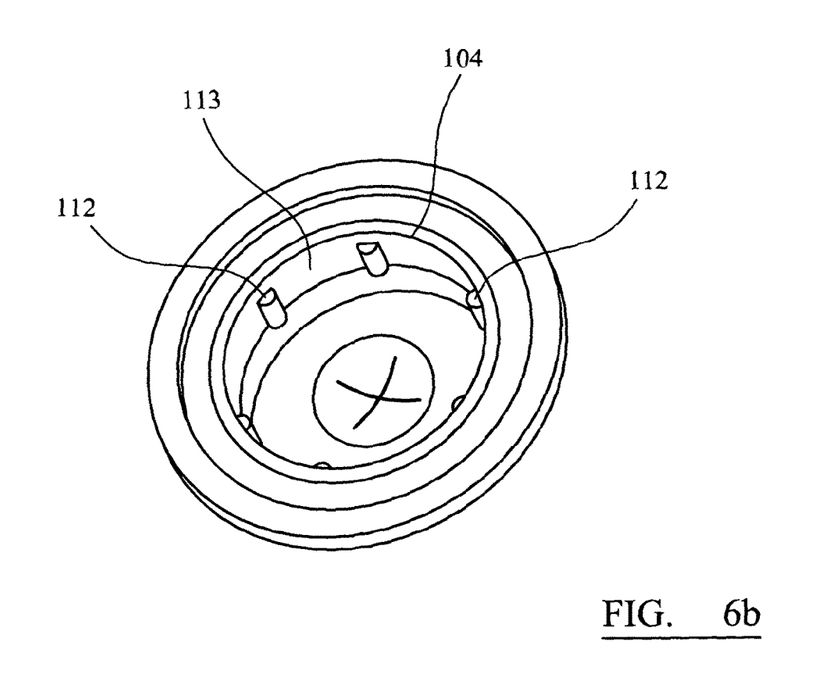

Referring to FIGS. 6a and 6b, the valve member of the invention is provided with a plurality of circumferential spaced apart pimples (112) on the inside surface (113) of the wall (104) of the valve member (103). When the valve is urged to an open position, the pimples (112) react against distortion of the side wall and therefore urge the valve back to a closed position. Thus a pressure differential is essential to reopen the valve member of the invention.

Referring to FIGS. 7a to 7d, 8a and 8b, the medicament container 2 (member 9, cavity 10 and sleeve 11) is loaded into a barrel 13 of a filling device or mechanism 14. In FIG. 7a the upper surface of member 9 has a radius to correspond with the radius of barrel 13, the barrel 13 is rotated to align the cavity 10 in member 9 (FIG. 7b) with hopper 15, medicament powder 12 contained in hopper 15 fills cavity 10. In FIG. 5c barrel 13 is further rotated, the surface 16 of barrel 13 closes off hopper 15, the surface 16 of the barrel housing 17 closes off cavity 17, retaining the powder.

Member 9 is then pushed through sleeve 1 so that sleeve 11 sits covering cavity 10 (note, shown as schematic from position b and c in FIG. 7). The barrel 13 is further rotated to facilitate the removal of the filled sub-assembly 3.

It will be appreciated that the foregoing description is limited to describing the progress of one sub-assembly 3 through the filling mechanism, in practice the barrel 13 would facilitate a number of sub-assemblies 3 at a time in a continuous process.

Figure 10A:
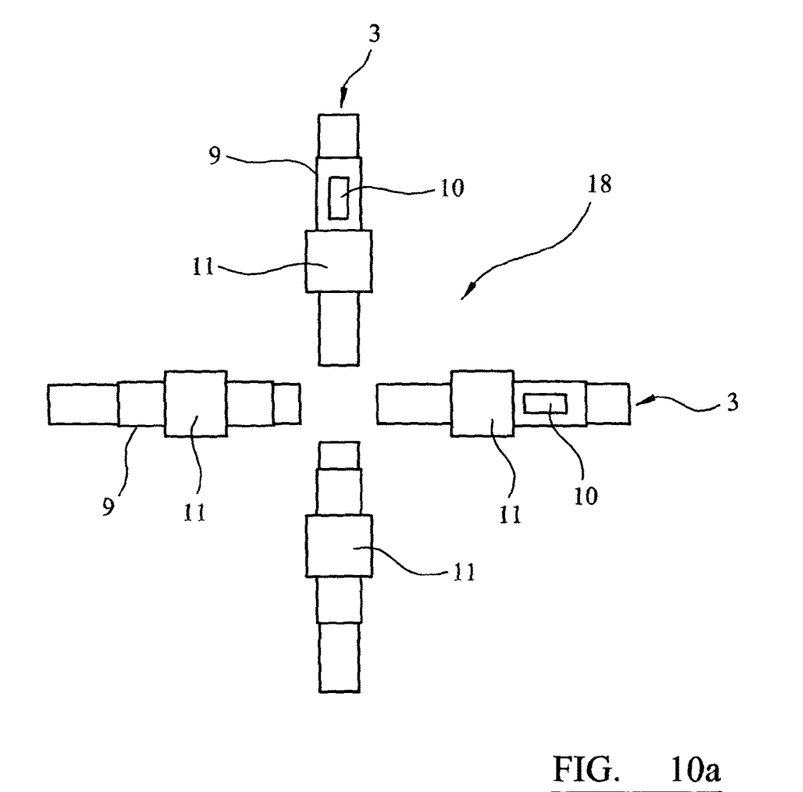
FIGS. 10a and 10b are schematic representations of the unit dose medicament container being filled by an alternative filling method.
Figure 10B:
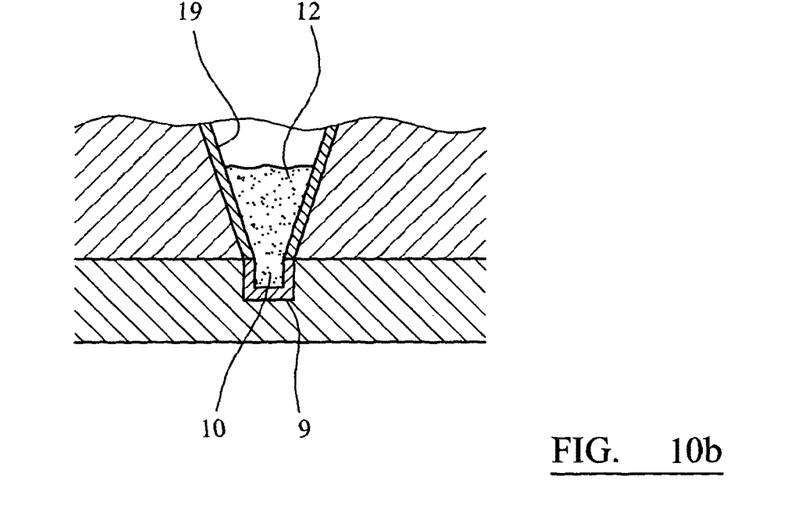

Referring to FIGS. 10a and 10b, in another embodiment of a filling device and method, the sub-assembly 3 is loaded into a disc 18. The upper surface of member 9 is flat (not shown) the disc 18 is rotated to align the cavity 10 in member 9 with hopper 19, the medicament powder 12 contained in hopper 19 fills cavity 10. Disc 18 is further rotated and the surface of disc 18 closes off the cavity 10, retaining the medicament powder 12. Member 9 is then pushed through sleeve 11 so that sleeve 11 sits covering cavity 10. The disc 18 is further rotated to facilitate the removal of the filled sub-assembly 4.

The above two descriptions of filling devices and methods are by way of example only, it will be appreciated that those skilled in the art will identify variations to these basic descriptions, for example by adding means of automation.

Referring to FIGS. 11a and 11b, the medicament device 20, for use in infusion, is assembled from four parts, a main body assembly 21, a drug (dry powder) carrier 22, a drug cavity cover sleeve 23 and a seal component 24.

These four parts are desirably assembled as two sub assemblies:

(a) the main body 21 and the seal 24; and
(b) the drug carrier 22 and cover sleeve 23.

The main body assembly 21 is a dispensing assembly comprising a body 25, a nozzle 26 and fluid/powder channels 27 and 28. The nozzle 26 is provided with lockable ends 29 and 30. In the embodiment shown, end 29 comprises a standard male luer lock and end 30 comprises a standard female luer lock.

The invention claimed is:

1. A dry powder medicament delivery device comprising: a medicament container containing a unit dose of dry powder medicament; a medicament dispensing assembly; and optionally an air source; wherein said medicament container comprises i) an elongate member provided with airways; ii) an inset cavity which acts as a medicament reservoir and iii) a slidable outer closure sleeve, wherein a sliding action of the outer closure sleeve reveals some or the entire cavity and aligns the cavity with the airways; the container provides a non-linear pathway for the flow of the powdered medicament; and the medicament powder is caused to substantially flow via the pathway which comprises at least two right angled turns as the medicament powder is expelled from the delivery device.

2. A dry powder medicament delivery device according to claim 1 wherein the device includes an air source.

3. A dry powder medicament delivery device according to claim 2 wherein the air source is a delivery pump.

4. A dry powder medicament delivery device according to claim 1 wherein the medicament dispensing assembly generally comprises a body and a nozzle.

5. A dry powder medicament delivery device according to claim 1 wherein the medicament dispensing assembly comprises an intranasal delivery device.

6. A dry powder medicament delivery device according to claim 3 wherein the delivery pump is a syringe.

7. A dry powder medicament delivery device according to claim 3 wherein the air source or delivery pump is a bellows.

8. A dry powder medicament delivery device according to claim 3 wherein the air source or delivery pump is a squeezable bulb.

9. A dry powder medicament delivery device according to claim 3 wherein the delivery pump comprises an air source and is provided with a bursting diaphragm or dispensing valve.

10. A dry powder medicament delivery device according to claim 1 wherein the device is adapted to facilitate application of the medicament in dry powder form via an air flow to a body orifice.

11. A dry powder medicament delivery device according to claim 1 wherein the device is an inhaler.

12. A dry powder medicament delivery device according to claim 11 wherein the delivery device is a nasal dry powder inhaler.

13. A dry powder medicament delivery device according to claim 1 wherein the dry powder medicament delivery device is for the delivery of a therapeutically effective amount of glucagon to a diabetic experiencing a hypoglycaemic reaction.

14. A dry powder medicament delivery device according to claim 1 wherein the device is suitable for the delivery of one or more dry powder vaccines.

15. A method of delivering a medicament to a patient which comprises the use of a dry powder medicament delivery device comprising: a medicament container containing a unit dose of dry powder medicament; a medicament dispensing assembly; and optionally an air source; wherein said medicament container comprises i) an elongate member provided with airways; ii) an inset cavity which acts as a medicament reservoir and iii) a slidable outer closure sleeve, wherein a sliding action of the outer closure sleeve reveals some or the entire cavity and aligns the cavity with the airways; the container provides a non-linear pathway for the flow of the powdered medicament and the medicament powder is caused to substantially flow via the pathway which comprises at least two right angled turns as the medicament powder is expelled from the delivery device.

16. A method of treatment of a patient with a disorder or prevention of a disorder which comprises the administration to the patient of a suitable medicament using a medicament delivery device according to claim 15.

* * * * *